(12) United States Patent
Bechtel et al.

(10) Patent No.: US 12,390,117 B2
(45) Date of Patent: *Aug. 19, 2025

(54) OPTICAL SENSOR MODULE FOR SPECKLEPLETHYSMOGRAPHY (SPG) AND PHOTOPLETHYSMOGRAPHY (PPG)

(71) Applicant: ROCKLEY PHOTONICS LIMITED, Altrincham (GB)

(72) Inventors: Kate LeeAnn Bechtel, Pleasant Hill, CA (US); James McMillan, Santa Monica, CA (US); Farzaneh Afshinmanesh, Pasadena, CA (US); Cody Dunn, Costa Mesa, CA (US)

(73) Assignee: Rockley Photonics Limited, Altrincham (GB)

( * ) Notice: Subject to any disclaimer, the term of this patent is extended or adjusted under 35 U.S.C. 154(b) by 413 days.

This patent is subject to a terminal disclaimer.

(21) Appl. No.: 17/711,974

(22) Filed: Apr. 1, 2022

(65) Prior Publication Data

US 2023/0148885 A1 May 18, 2023

Related U.S. Application Data

(60) Provisional application No. 63/279,932, filed on Nov. 16, 2021.

(51) Int. Cl.
*A61B 5/024* (2006.01)
*A61B 5/00* (2006.01)
*A61B 5/0295* (2006.01)

(52) U.S. Cl.
CPC ...... *A61B 5/02433* (2013.01); *A61B 5/02438* (2013.01); *A61B 5/0295* (2013.01); *A61B 5/681* (2013.01)

(58) Field of Classification Search
None
See application file for complete search history.

(56) References Cited

U.S. PATENT DOCUMENTS 5,243,983 A 9/1993 Tarr et al.
5,830,132 A 11/1998 Robinson
(Continued)

FOREIGN PATENT DOCUMENTS

CN 108709847 A 10/2018
CN 110301896 B 10/2019
(Continued)

OTHER PUBLICATIONS

Akram, M. N. et al., "Laser speckle reduction due to spatial and angular diversity introduced by fast scanning micromirror", Applied Optics, Jun. 4, 2010, pp. 3297-3304, vol. 49, No. 17, Optical Society of America.

(Continued)

*Primary Examiner* — Jonathan T Kuo
(74) *Attorney, Agent, or Firm* — Womble Bond Dickinson (US) LLP

(57) ABSTRACT

An optical sensor module for measuring both specklepl-ethysmography (SPG) and photoplethysmography (PPG) signals at human or animal tissue, the optical sensor module comprising: a first light source, for illuminating the tissue for use with SPG measurements, the first light source comprising a laser; a second light source, for illuminating the tissue for use with PPG measurements; and one or more optical sensor(s) for receiving light from the illuminated tissue.

13 Claims, 17 Drawing Sheets

(56) References Cited

U.S. PATENT DOCUMENTS

| | | | |
|---|---|---|---|
| 6,246,892 B1 | 6/2001 | Chance | |
| 6,560,478 B1 | 5/2003 | Alfano et al. | |
| 6,919,549 B2 | 7/2005 | Bamji et al. | |
| 7,035,679 B2 | 4/2006 | Addison et al. | |
| 7,113,817 B1 | 9/2006 | Winchester, Jr. et al. | |
| 7,250,317 B2 | 7/2007 | Heideman | |
| 7,295,783 B2 | 11/2007 | Singh et al. | |
| 7,375,812 B2 | 5/2008 | Atia et al. | |
| 7,505,128 B2 | 3/2009 | Zribi et al. | |
| 7,761,126 B2 | 7/2010 | Gardner et al. | |
| 7,865,225 B2 | 1/2011 | Kaltschmidt et al. | |
| 7,922,664 B2 | 4/2011 | Elliott | |
| 7,925,056 B2 | 4/2011 | Presura et al. | |
| 8,237,927 B1 | 8/2012 | Reeve et al. | |
| 8,277,384 B2 | 10/2012 | Fine | |
| 8,313,439 B2 | 11/2012 | McCombie et al. | |
| 8,343,062 B2 | 1/2013 | Fortin et al. | |
| 8,343,063 B2 | 1/2013 | Borgos | |
| 8,376,955 B2 | 2/2013 | Baker, Jr. | |
| 8,398,556 B2 | 3/2013 | Sethi et al. | |
| 8,868,149 B2 | 10/2014 | Eisen et al. | |
| 8,920,332 B2 | 12/2014 | Hong et al. | |
| 8,923,942 B2 | 12/2014 | Bernreuter | |
| 8,945,017 B2 | 2/2015 | Venkatraman et al. | |
| 8,948,832 B2 | 2/2015 | Hong et al. | |
| 8,956,303 B2 | 2/2015 | Hong et al. | |
| 8,998,815 B2 | 4/2015 | Venkatraman et al. | |
| 9,005,129 B2 | 4/2015 | Venkatraman et al. | |
| 9,113,794 B2 | 8/2015 | Hong et al. | |
| 9,113,795 B2 | 8/2015 | Hong et al. | |
| 9,149,216 B1 | 10/2015 | Eisen et al. | |
| 9,155,480 B2 | 10/2015 | Thakor et al. | |
| 9,226,673 B2 | 1/2016 | Ferguson, Jr. et al. | |
| 9,237,855 B2 | 1/2016 | Hong et al. | |
| 9,307,917 B2 | 4/2016 | Hong et al. | |
| 9,494,567 B2 | 11/2016 | Islam | |
| 9,687,162 B2 | 6/2017 | Vetter et al. | |
| 9,704,050 B2 | 7/2017 | Lee et al. | |
| 9,730,622 B2 | 8/2017 | Eisen et al. | |
| 9,772,280 B2 | 9/2017 | Cerussi et al. | |
| 9,804,027 B2 | 10/2017 | Fish et al. | |
| 9,846,126 B2 | 12/2017 | Gunn, III et al. | |
| 9,848,787 B2 | 12/2017 | White et al. | |
| 9,877,681 B2 | 1/2018 | Silverman | |
| 9,931,040 B2 | 4/2018 | Homyk et al. | |
| 9,970,955 B1 | 5/2018 | Homyk et al. | |
| 10,004,406 B2 | 6/2018 | Yuen et al. | |
| 10,058,256 B2 | 8/2018 | Chen et al. | |
| 10,178,959 B1 | 1/2019 | Homyk et al. | |
| 10,178,973 B2 | 1/2019 | Venkatraman et al. | |
| 10,194,808 B1 | 2/2019 | Thompson et al. | |
| 10,206,576 B2 | 2/2019 | Shcherbakov et al. | |
| 10,215,698 B2 | 2/2019 | Han et al. | |
| 10,241,033 B2 | 3/2019 | Uematsu et al. | |
| 10,271,740 B2 | 4/2019 | Ward et al. | |
| 10,314,532 B2 | 6/2019 | Ward et al. | |
| 10,326,035 B2 | 6/2019 | Lu et al. | |
| 10,326,036 B2 | 6/2019 | Sweeney et al. | |
| 10,349,847 B2 | 7/2019 | Kwon et al. | |
| 10,352,768 B2 | 7/2019 | Simpkin et al. | |
| 10,357,165 B2 | 7/2019 | Yoon | |
| 10,422,693 B2 | 9/2019 | Fish et al. | |
| 10,451,537 B2 | 10/2019 | Nakaji | |
| 10,463,286 B2 | 11/2019 | Schenkman et al. | |
| 10,492,684 B2 | 12/2019 | Khachaturian et al. | |
| 10,506,926 B2 | 12/2019 | Khachaturian et al. | |
| 10,506,955 B2 | 12/2019 | Tholl et al. | |
| 10,568,527 B2 | 2/2020 | Yoon et al. | |
| 10,588,519 B2 | 3/2020 | Yuen et al. | |
| 10,602,987 B2 | 3/2020 | Khachaturian et al. | |
| 10,627,849 B1 | 4/2020 | Scofield et al. | |
| 10,641,962 B2 | 5/2020 | Nykänen et al. | |
| 10,643,903 B2 | 5/2020 | Drake et al. | |
| 10,667,688 B2 | 6/2020 | Khachaturian et al. | |
| 10,677,989 B2 | 6/2020 | Abediasl et al. | |
| 10,681,259 B2 | 6/2020 | Ichiki et al. | |
| 10,681,283 B2 | 6/2020 | Nakashima et al. | |
| 10,694,997 B2 | 6/2020 | Kim et al. | |
| 10,718,668 B2 | 7/2020 | Gu et al. | |
| 10,722,177 B2 | 7/2020 | Homyk et al. | |
| 10,739,256 B1 | 8/2020 | Rickman et al. | |
| 10,750,956 B2 | 8/2020 | Zalevsky et al. | |
| 10,775,239 B2 | 9/2020 | Lee et al. | |
| 10,813,597 B2 | 10/2020 | Rice et al. | |
| 10,820,858 B2 | 11/2020 | Yoon et al. | |
| 10,842,422 B2 | 11/2020 | Yu et al. | |
| 10,871,503 B1 | 12/2020 | Homyk et al. | |
| 10,966,616 B2 | 4/2021 | De Morree et al. | |
| 10,973,422 B2 | 4/2021 | Pantelopoulos et al. | |
| 11,022,751 B2 | 6/2021 | Bauters et al. | |
| 11,045,103 B2 | 6/2021 | Shchekin et al. | |
| 11,079,364 B2 | 8/2021 | Leger et al. | |
| 11,096,601 B2 | 8/2021 | Hong et al. | |
| 11,096,608 B2 | 8/2021 | Van Dorpe et al. | |
| 11,129,544 B2 | 9/2021 | Zalevsky et al. | |
| 11,202,582 B2 | 12/2021 | Verkruijsse et al. | |
| 11,213,217 B2 | 1/2022 | Han et al. | |
| 11,278,220 B2 | 3/2022 | Tucker et al. | |
| 11,298,035 B2 | 4/2022 | Huijbregts et al. | |
| 11,369,275 B2 | 6/2022 | Song et al. | |
| 11,445,922 B2 | 9/2022 | Naima | |
| 11,553,851 B2 | 1/2023 | Kim et al. | |
| 11,583,185 B2 | 2/2023 | Homyk et al. | |
| 11,666,238 B2 | 6/2023 | Rege et al. | |
| 11,666,277 B2 | 6/2023 | Yoon et al. | |
| 11,684,281 B2 | 6/2023 | Pantelopoulos et al. | |
| 11,690,513 B2 | 7/2023 | Hu et al. | |
| 11,696,693 B2 | 7/2023 | Wong | |
| 11,709,120 B2 | 7/2023 | Rice et al. | |
| 11,744,491 B2 | 9/2023 | Dunn et al. | |
| 11,751,811 B2 | 9/2023 | Sun et al. | |
| 11,759,116 B2 | 9/2023 | White et al. | |
| 11,759,121 B2 | 9/2023 | Mccann et al. | |
| 11,771,343 B2 | 10/2023 | Sacha | |
| 11,800,990 B2 | 10/2023 | White et al. | |
| 11,857,301 B1 | 1/2024 | Homyk et al. | |
| 11,883,134 B2 | 1/2024 | Leabman | |
| 11,890,081 B2 | 2/2024 | Jang | |
| 11,980,451 B2 | 5/2024 | Albert | |
| 2002/0068859 A1* | 6/2002 | Knopp | A61B 5/1455 600/322 |
| 2005/0249509 A1 | 11/2005 | Nagarajan et al. | |
| 2006/0124829 A1 | 6/2006 | Song et al. | |
| 2006/0204175 A1 | 9/2006 | Laurent-Lund et al. | |
| 2008/0204752 A1 | 8/2008 | Dorvee et al. | |
| 2008/0220512 A1 | 9/2008 | Koh et al. | |
| 2008/0316567 A1 | 12/2008 | Grasser et al. | |
| 2011/0054277 A1 | 3/2011 | Pinter et al. | |
| 2011/0082355 A1 | 4/2011 | Eisen et al. | |
| 2011/0196244 A1 | 8/2011 | Ribas Ripoll et al. | |
| 2012/0130215 A1 | 5/2012 | Fine et al. | |
| 2013/0131475 A1 | 5/2013 | Eisen et al. | |
| 2013/0190630 A1 | 7/2013 | Borgos | |
| 2014/0094666 A1 | 4/2014 | Fine | |
| 2014/0200423 A1 | 7/2014 | Eisen et al. | |
| 2014/0316286 A1 | 10/2014 | Addison et al. | |
| 2014/0376001 A1 | 12/2014 | Swanson | |
| 2015/0157224 A1 | 6/2015 | Carmon et al. | |
| 2015/0196251 A1 | 7/2015 | Outwater et al. | |
| 2015/0201854 A1 | 7/2015 | Hong et al. | |
| 2016/0066790 A1 | 3/2016 | Shcherbakov et al. | |
| 2016/0106327 A1 | 4/2016 | Yoon et al. | |
| 2016/0157736 A1 | 6/2016 | Huang et al. | |
| 2016/0161685 A1 | 6/2016 | Xu et al. | |
| 2016/0266337 A1 | 9/2016 | Feng | |
| 2016/0278676 A1 | 9/2016 | Eisen et al. | |
| 2016/0282265 A1 | 9/2016 | Su et al. | |
| 2016/0287107 A1 | 10/2016 | Szabados et al. | |
| 2017/0014037 A1 | 1/2017 | Coppola et al. | |
| 2017/0065184 A1 | 3/2017 | Barak | |
| 2017/0108439 A1 | 4/2017 | Stievater et al. | |
| 2017/0138789 A1 | 5/2017 | Ivanov | |
| 2017/0231513 A1* | 8/2017 | Presura | A61B 5/024 600/301 |

(56) References Cited

U.S. PATENT DOCUMENTS

| | | |
|---|---|---|
| 2017/0315292 A1 | 11/2017 | Mullen et al. |
| 2018/0045566 A1 | 2/2018 | Fish et al. |
| 2018/0064399 A1* | 3/2018 | Buettgen ............ A61B 5/02416 |
| 2018/0110423 A1 | 4/2018 | Presura et al. |
| 2018/0160913 A1 | 6/2018 | Fine |
| 2018/0238794 A1 | 8/2018 | Kangas et al. |
| 2018/0263519 A1 | 9/2018 | Gu |
| 2018/0283950 A1 | 10/2018 | Ge et al. |
| 2018/0296168 A1 | 10/2018 | Rice et al. |
| 2019/0005351 A1* | 1/2019 | Zhou ................ G01N 15/1459 |
| 2019/0046056 A1 | 2/2019 | Khachaturian et al. |
| 2019/0053721 A1 | 2/2019 | Boas et al. |
| 2019/0094009 A1 | 3/2019 | Aizawa et al. |
| 2019/0167118 A1 | 6/2019 | Vilenskii et al. |
| 2019/0175030 A1 | 6/2019 | Verkruijsse et al. |
| 2019/0336006 A1 | 11/2019 | Horstmeyer et al. |
| 2019/0343442 A1 | 11/2019 | Aung et al. |
| 2019/0343456 A1 | 11/2019 | Kahlert et al. |
| 2019/0387972 A1 | 12/2019 | Hu et al. |
| 2019/0391243 A1 | 12/2019 | Nicolaescu |
| 2019/0391702 A1 | 12/2019 | Jo et al. |
| 2020/0003619 A1 | 1/2020 | Hu et al. |
| 2020/0069225 A1 | 3/2020 | Vizbaras et al. |
| 2020/0158548 A1 | 5/2020 | Rice et al. |
| 2020/0196874 A1 | 6/2020 | Rozental et al. |
| 2020/0214602 A1 | 7/2020 | Narumi et al. |
| 2020/0359948 A1 | 11/2020 | Dunn et al. |
| 2020/0397351 A1 | 12/2020 | Miyata |
| 2021/0000385 A1 | 1/2021 | Warren et al. |
| 2021/0022623 A1* | 1/2021 | Rice ................ A61B 5/02116 |
| 2021/0028602 A1 | 1/2021 | Cao et al. |
| 2021/0267471 A1 | 9/2021 | Bonomi et al. |
| 2021/0386310 A1 | 12/2021 | Hong et al. |
| 2022/0015649 A1 | 1/2022 | Ikuta et al. |
| 2022/0019861 A1 | 1/2022 | Durr et al. |
| 2022/0039679 A1 | 2/2022 | Califa et al. |
| 2022/0265158 A1 | 8/2022 | Tokura |
| 2022/0370010 A1 | 11/2022 | Zilkie et al. |
| 2022/0413143 A1 | 12/2022 | Parsa et al. |
| 2023/0003938 A1 | 1/2023 | Zilkie et al. |
| 2023/0039055 A1 | 2/2023 | Gardner et al. |
| 2023/0087295 A1 | 3/2023 | Dunn et al. |
| 2023/0148885 A1 | 5/2023 | Bechtel et al. |
| 2023/0148886 A1 | 5/2023 | Bechtel et al. |
| 2023/0277075 A1 | 9/2023 | Pantelopoulos et al. |
| 2023/0320598 A1 | 10/2023 | Khine et al. |
| 2023/0347029 A1 | 11/2023 | Corso et al. |
| 2023/0397818 A1 | 12/2023 | Newhouse et al. |
| 2023/0401747 A1 | 12/2023 | Dunn et al. |
| 2024/0041342 A1 | 2/2024 | Lai et al. |
| 2024/0074667 A1 | 3/2024 | Rick et al. |
| 2024/0108289 A1 | 4/2024 | Bechtel et al. |
| 2024/0115212 A1 | 4/2024 | Jang |
| 2024/0156355 A1 | 5/2024 | O'Brien et al. |

FOREIGN PATENT DOCUMENTS

| | | |
|---|---|---|
| CN | 211094079 U | 7/2020 |
| CN | 211131004 U | 7/2020 |
| EP | 3 002 568 A1 | 4/2016 |
| EP | 2 395 958 B1 | 12/2017 |
| EP | 3 384 841 A1 | 10/2018 |
| EP | 3 558 119 B1 | 11/2020 |
| EP | 3 886 686 | 10/2021 |
| WO | WO 2018/029123 A1 | 2/2018 |
| WO | WO 2019/149815 A1 | 8/2019 |
| WO | WO 2019/233903 A1 | 12/2019 |
| WO | WO 2020/030641 A1 | 2/2020 |
| WO | WO 2020/114989 A1 | 6/2020 |
| WO | WO 2021/058338 A1 | 4/2021 |
| WO | WO 2021/094473 A1 | 5/2021 |
| WO | WO 2021/116766 A1 | 6/2021 |
| WO | WO 2021/116766 A8 | 6/2021 |
| WO | WO 2023/245149 A2 | 12/2023 |
| WO | WO 2024/052289 A1 | 3/2024 |

OTHER PUBLICATIONS

Baek, H. J. et al., "The Effect of Optical Crosstalk on Accuracy of Reflectance-Type Pulse Oximeter for Mobile Healthcare", Journal of Healthcare Engineering, Oct. 21, 2018, 9 pages, vol. 2018, Article ID 3521738, Hindawi, https://doi.org/10.1155/2018/3521738.

Baets, R. et al., "Spectroscopy-on-chip applications of silicon photonics", Proc. Of SPIE, 2013, pp. 86270I-1 through 86270I-10, vol. 8627, SPIE.

Berger, A. J. et al., "Feasibility of measuring blood glucose concentration by near-infrared Raman spectroscopy", Spectrochimica Acta Part A, 1997, pp. 287-292, Elsevier Science B.V.

Bi, R. et al., "A speckle-based method for fast blood flow measurement in deep tissue", Proceedings of SPIE, Optical Biopsy XIX: Toward Real-Time Spectroscopic Imaging and Diagnosis, Mar. 5, 2021, pp. 1163606-1 through 1163606-5, vol. 11636, SPIE.

Biswas, A. et al., "Fast diffuse correlation spectroscopy with a low-cost, fiber-less embedded diode laser", Biomedical Optics Express, Oct. 4, 2021, pp. 6686-6700, vol. 12, No. 11, Optical Society of America.

Brouckaert, J. et al., "Silicon-on-Insulator Microspectrometer", Proceedings Symposium IEEE/LEOS Benelux Chapter, 2008, pp. 7-10, IEEE.

Cole, D. B. et al., "Integrated heterodyne interferometer with on-chip modulators and detectors", Optics Letters, Jun. 25, 2015, pp. 3097-3100, vol. 40, No. 13, Optical Society of America.

Epping, J. P. et al., "High power, tunable, narrow linewidth dual gain hybrid laser", Laser Congress, Oct. 3, 2019, pp. 1-2.

Fu, D. et al., "In Vivo Metabolic Fingerprinting of Neutral Lipids with Hyperspectral Stimulated Raman Scattering Microscopy", Journal of the American Chemical Society, May 28, 2014, pp. 8820-8828, American Chemical Society Publications.

Fukui, T. et al., "Single-Pixel Imaging Using Multimode Fiber and Silicon Photonic Phased Array", Journal of Lightwave Technology, Jul. 14, 2020, pp. 839-844, vol. 39, No. 3, IEEE.

Gottschling, K. et al., "Molecular Insights into Carbon Dioxide Sorption in Hydrazone-Based Covalent Organic Frameworks with Tertiary Amine Moieties", Chemistry of Materials, Feb. 13, 2019, pp. 1946-1955, American Chemical Society.

Hashimoto, Y. et al., "Fabrication of an Anti-Reflective and Super-Hydrophobic Structure by Vacuum Ultraviolet Light-Assisted Bonding and Nanoscale Pattern Transfer", Micromachines, Apr. 15, 2018, pp. 1-11, www.mdpi.com/journal/micromachines.

Hollis, V. S. et al., "Non-invasive monitoring of brain tissue temperature by near-infrared spectroscopy", Proceedings of SPIE, Optical Tomography and Spectroscopy of Tissue IV, Jun. 29, 2001, pp. 470-481, vol. 4250, SPIE, https://www.spiedigitallibrary.org/conference-proceedings-of-spie/4250/1/Noninvasive-monitoring-of-brain-tissue-temperature-by-near-infrared-spectroscopy/10.1117/12.434506.short?SSO=1.

International Search Report and Written Opinion of the International Searching Authority, Mailed Mar. 11, 2021, Corresponding to PCT/IB2020/001037, 13 pages.

International Search Report and Written Opinion of the International Searching Authority, mailed Apr. 4, 2023, corresponding to PCT/EP2022/082341, 33 pages.

International Search Report and Written Opinion of the International Searching Authority, mailed Feb. 1, 2022, corresponding to PCT/IB2021/000649, 18 pages.

International Search Report and Written Opinion of the International Searching Authority, mailed Nov. 15, 2021, corresponding to PCT/IB2021/000517, 15 pages.

International Search Report and Written Opinion of the International Searching Authority, mailed Oct. 10, 2022, corresponding to PCT/IB2022/000373, 16 pages.

International Search Report and Written Opinion of the International Searching Authority, mailed Oct. 19, 2022, corresponding to PCT/EP2022/071467, 16 pages.

Invitation to Pay Additional Fees and Partial Search Report mailed Feb. 14, 2023 in related International Application No. PCT/EP2022/082341, 18 pages.

(56) References Cited

OTHER PUBLICATIONS

Izutsu, M. et al., "Integrated Optical SSB Modulator/Frequency Shifter", IEEE Journal of Quantum Electronics, Nov. 1981, pp. 2225-2227, vol. QE-17, No. 11, IEEE.
Kang, J. W. et al., "Direct observation of glucose fingerprint using in vivo Raman spectroscopy," Science Advances, Jan. 24, 2020, pp. 1-8, American Association for the Advancement of Science.
Karlsson, C. J. et al., "All-fiber multifunction continuous-wave coherent laser radar at 1.55 µm for range, speed, vibration, and wind measurements", Applied Optics, Jul. 20, 2000, pp. 3716-3726, vol. 39, No. 21, Optical Society of America.
Lai, N. et al., "CO2 Capture With Absorbents of Tertiary Amine Functionalized Nano-SiO2", Frontiers in Chemistry, Feb. 28, 2020, pp. 1-9, vol. 8, Article 146, www.frontiersin.org.
Lapchuk, A. et al., "Investigation of speckle suppression beyond human eye sensitivity by using a passive multimode fiber and a multimode fiber bundle", Applied Optics, Feb. 21, 2020, pp. 6820-6834, vol. 28, No. 5, Optical Society of America.
Loi, R. et al., "Transfer Printing of AlGaInAs/InP Etched Facet Lasers to Si Substrates", IEEE Photonics Journal, Nov. 11, 2016, 11 pages, vol. 8, No. 6, IEEE.
Mehta, D. S. et al., "Laser speckle reduction by multimode optical fiber bundle with combined temporal, spatial, and angular diversity", Applied Optics, Apr. 11, 2012, pp. 1894-1904, vol. 51, No. 12, Optical Society of America.
Merritt, S. et al., "Monitoring temperature non-invasively using broadband Diffuse Optical Spectroscopy", OSA/FIO, 2004, 1 page, Optical Society of America, https://opg.optica.org/abstract.cfm?URI=FiO-2004-FTuK4.
Noriki, A. et al., "45-degree curved micro-mirror for vertical optical I/O of silicon photonics chip", Optics Express, Jul. 1, 2019, pp. 19749-19757, vol. 27, No. 14, Optical Society of America, https://doi.org/10.1364/OE.27.019749.
Poulton, C. V. et al., "Frequency-modulated Continuous-wave LIDAR Module in Silicon Photonics", OFC, 2015, 4 pages, Optical Society of America.
Redding, B. et al., "Compact spectrometer based on a disordered photonic chip", Nature Photonics, Jul. 28, 2013, pp. 746-751, vol. 7, Macmillan Publishers Limited.
Redding, B. et al., "Evanescently coupled multimode spiral spectrometer", Optica, Aug. 25, 2016, pp. 956-962, vol. 3, No. 9, Optical Society of America.
Robinson, M. B., "Interferometric diffuse correlation spectroscopy improves measurements at long source-detector separation and low photon count rate", Journal of Biomedical Optics, Sep. 30, 2020, pp. 097004-1 through 097004-12, vol. 25, No. 9, SPIE.
Roelkens, G. et al., "Transfer printing for silicon photonics transceivers and interposers", 2018 IEEE Optical Interconnects Conference, Jun. 4, 2018, pp. 13-14, IEEE.
Ryckeboer, E., "Spectroscopic Detection of Glucose with a Silicon Photonic Integrated Circuit", Universiteit Gent, Jan. 1, 2014, 263 pages, ISBN 978-90-8578-688-7, http://www.photonics.intec.ugent.be/download/phd_206.pdf.
Schneider, S. et al., "Optical coherence tomography system mass-producible on a silicon photonic chip", Optics Express, Jan. 20, 2016, pp. 1573-1586, vol. 24, No. 2, Optical Society of America.
Shimotsu, S. et al., "Single Side-Band Modulation Performance of a LiNbO3 Integrated Modulator Consisting of Four-Phase Modulator Waveguides", IEEE Photonics Technology Letters, Apr. 2001, pp. 364-366, vol. 13, No. 4, IEEE.
Subramanian, A. Z. et al., "Silicon and silicon nitride photonic circuits for spectroscopic sensing on-a-chip [Invited]", Photon. Res., Aug. 28, 2015, pp. B47-B59, vol. 3, No. 5, Chinese Laser Press.
Timm, U. et al., "Non-Invasive Optical Real-time Measurement of Total Hemoglobin Content", Procedia Engineering, 2010, pp. 488-491, Elsevier Ltd.
Tran, T-T-K. et al., "Speckle reduction in laser projection displays through angle and wavelength diversity", Applied Optics, Feb. 16, 2016, pp. 1267-1274, vol. 55, No. 6, Optical Society of America.
Tuchin, V., "Chapter 8: Coherent Effects at the Interaction of Laser Radiation with Tissues and Cell Flows", Tissue Optics Light Scattering Methods and Instruments for Medical Diagnostics, 3rd Edition, 2015, pp. 359-417, SPIE.
U.S. Appl. No. 18/019,085, filed Jan. 31, 2023.
U.S. Appl. No. 18/027,881, filed Mar. 22, 2023.
U.S. Appl. No. 18/056,666, filed Nov. 17, 2022.
U.S. Notice of Allowance from U.S. Appl. No. 17/757,130, dated Jan. 18, 2023, 10 pages.
Valley, G.C. et al., "Multimode waveguide speckle patterns for compressive sensing", Optics Letters, May 23, 2016, pp. 2529-2532, vol. 41, No. 11, Optical Society of America.
Van Gastel, M. et al., "Camera-based pulse-oximetry—validated risks and opportunities from theoretical analysis", Biomedical Optics Express, Dec. 5, 2017, pp. 102-119, vol. 9, No. 1, Optical Society of America.
Website: "Optical Solutions", Molex, dated 2023, printed May 10, 2023, 13 pages, Molex, LLC, https://www.molex.com/en-us/products/optical-solutions.
Website: "Track Your SpO2 to Uncover Changes in Your Wellbeing", Fitbit News, dated Sep. 7, 2020, printed Apr. 17, 2023, 7 pages, Fitbit, Inc., https://blog.fitbit.com/track-your-spo2/).626.
Wenz, J. J., "Examining water in model membranes by near infrared spectroscopy and multivariate analysis", BBA—Biomembranes, Dec. 9, 2017, pp. 673-682, Elsevier B.V., https://www.sciencedirect.com/science/article/pii/S0005273617303905.
Xu, M. et al., "Laser Speckle Reduction Using a Motionless Despeckle Element Based on Random Mie Scattering", Journal of Display Technology, Nov. 12, 2013, pp. 151-156, vol. 10, No. 2, IEEE.
Yamakoshi, Y. et al., "Side-scattered finger-photoplethysmography: experimental investigations toward practical noninvasive measurement of blood glucose", Journal of Biomedical Optics, Jun. 2017, pp. 067001-1 through 067001-11, vol. 22, No. 6, SPIE.
Yao, Z. et al., "Integrated Silicon Photonic Microresonators: Emerging Technologies", IEEE Journal of Selected Topics in Quantum Electronics, Jun. 11, 2018, 24 pages, vol. 24, No. 6, IEEE.
Zhang, J. et al., "III-V-on-Si photonic integrated circuits realized using micro-transfer-printing", APL Photonics, Nov. 4, 2019, pp. 110803-1 through 110803-10.
Zijlstra, W. G. et al., "Absorption Spectra of Human Fetal and Adult Oxyhemoglobin, De-Oxyhemoglobin, Carboxyhemoglobin, and Methemoglobin", Clinical Chemistry, Sep. 1991, pp. 1633-1638, vol. 37, No. 9, https://academic.oup.com/clinchem/article-abstract/37/9/1633/5649610?redirectedFrom=fulltext.
Zilkie, A. J. et al., "Multi-Micron Silicon Photonics Platform for Highly Manufacturable and Versitile Photonic Integrated Circuits", IEEE Journal of Selected Topics in Quantum Electronics, Apr. 15, 2019, 13 pages, vol. 25, No. 5, IEEE.
Zilkie, A. J. et al., "Power-efficient III-V/Silicon external cavity DBR lasers", Optics Express, Sep. 27, 2012, pp. 23456-23462, vol. 20, No. 21, Optical Society of America.
U.S. Appl. No. 18/667,608, filed May 17, 2024.
U.S. Office Action from U.S. Appl. No. 17/934,502, dated Aug. 31, 2023, 6 pages.
U.S. Office Action from U.S. Appl. No. 17/934,502, dated Feb. 1, 2024, 6 pages.
Ge, Z. et al., "Dynamic laser speckle analysis using the event sensor", Applied Optics, Dec. 23, 2020, pp. 172-178, vol. 60, No. 1, Optical Society of America.
Ghijsen, M. et al., "Wearable speckle plethysmography (SPG) for characterizing microvascular flow and resistance", Biomedical Optics Express, Jul. 30, 2018, pp. 3937-3952, vol. 9, No. 8, Optical Society of America under the terms of the OSA Open Access Publishing Agreement.
International Search Report and Written Opinion of the International Searching Authority, mailed Feb. 14, 2023, corresponding to PCT/EP2022/082162, 33 pages.
Lai, M. et al., "Perfusion Monitoring by Contactless Photoplethysmography Imaging", 2019 IEEE 16th International Symposium on Biomedical Imaging (ISBI 2019), Venice, Italy, Apr. 8-11, 2019, pp. 1778-1782, IEEE.

(56) References Cited

OTHER PUBLICATIONS

Liu, X. et al., "Simultaneous measurements of tissue blood flow and oxygenation using a wearable fiber-free optical sensor", Journal of Biomedical Optics, Jan. 29, 2021, pp. 012705-1 through 012705-15, vol. 26, No. 1, SPIE.

Lu, H. et al., "Single-trial estimation of the cerebral metabolic rate of oxygen with imaging photoplethysmography and laser speckle contrast imaging", Optics Letters, Mar. 17, 2015, pp. 1193-1196, vol. 40, No. 7, Optical Society of America.

U.S. Appl. No. 17/934,502, filed Sep. 22, 2022.

U.S. Office Action from U.S. Appl. No. 17/934,502, dated Jun. 5, 2024, 7 pages.

* cited by examiner

OPTICAL SENSOR MODULE FOR SPECKLEPLETHYSMOGRAPHY (SPG) AND PHOTOPLETHYSMOGRAPHY (PPG)

CROSS-REFERENCE TO RELATED APPLICATIONS

The present application claims priority to and the benefit of U.S. Provisional Application No. 63/279,932, filed Nov. 16, 2021, entitled "A COMBINED OPTICAL SENSOR MODULE", the entire content of which is incorporated herein by reference.

FIELD

Embodiments of the present invention relate to an optical sensor, particularly to an optical sensor module for measuring both speckleplethysmography (SPG) and photoplethysmography (PPG) signals at human tissue.

BACKGROUND

Photoplethysmography (PPG) signals are currently utilized to extract cardiovascular parameters such as heart rate (HR), pulsatile oxygen saturation (SpO2) and blood pressure (BP). PPG signals arise from the change in tissue absorption caused by blood volume variation during pulsatile flow. These AC signals are generally of low magnitude as compared to a DC background. This is especially true on the wrist, where the pulsatile signal may be on the order of 0.4% or less than the measured intensity at red wavelengths. Red and near infra-red (NIR) light sources are required to obtain SpO2 values. Most wearables that provide SpO2 at wrist do so only during a person's quiescent periods, such as at night, where many pulses can be averaged in order to overcome low signal quality. To obtain daily beat-to-beat heartbeat values, many PPG modules include a green LED that has higher responsivity to changes in blood absorption. However, the green light does not penetrate very deeply and the signal quality is impacted by pressure that reduces circulation in the microvasculature. It is also undesirable for many people to observe a bright green light in a wearable device during the night.

Furthermore, it is possible that blood pressure may be extracted with more accuracy and reliability from blood flow data (speckleplethysmography, SPG) or a combination of blood flow and PPG than from PPG signals alone. For this reason, it is advantageous to simultaneously collect both SPG and PPG signals for the purposes of obtaining HR, HRV, SpO2, and BP measurements. To obtain SpO2, either or both of SPG and PPG may be collected from at least two wavelengths. For co-oximetry measurements in which more than one form of modified hemoglobin is measured, such as methemoglobin and carboxyhemoglobin, many more than 2 wavelengths may be utilized, often 6 or more.

It may be desirable to obtain a host of cardiovascular parameters from one compact, body-worn module. This may be achieved through the combination of SPG and PPG signals. Previously, researchers have demonstrated a combined system for measuring blood flow and tissue oxygenation by utilizing two laser diodes (red, NIR/IR) and a CMOS image sensor [Liu et al. J. Biomed. Opt. 26(1) 012705-1, 2021]. The calculation of SPG via spatial contrast measurements involves measuring both the standard deviation and intensity of the speckle image and calculating the ratio. Therefore, the calculation uses a PPG signal, which is directly related to the measured image intensity. However, this method is not optimal for resolving the pulsatile PPG signal at medium to low blood volumes, such as would be the case for a consumer wearable device. Indeed, the authors only demonstrated tissue oxygen saturation, StO2, which is not the resolved pulsatile SpO2 signal.

Systems that are optimized for PPG measurements in consumer wearables include DC and ambient light subtraction prior to amplifying the AC signal in order to improve dynamic range and sensitivity. Additionally, the photodiodes used are generally large format (e.g. 2×3 mm) to increase the number of detected photons. Finally, it is typical to use LEDs which, unlike lasers, do not produce speckle noise in intensity measurements.

SUMMARY

Accordingly, embodiments of the present invention aim to solve the above problems by providing, according to one or more embodiments of a first aspect, an optical sensor module for measuring both speckleplethysmography (SPG) and photoplethysmography (PPG) signals at human tissue, the optical sensor module comprising: a first light source, for illuminating the human tissue for use with SPG measurements, the first light source comprising a laser; a second light source, for illuminating the human tissue for use with PPG measurements; and one or more optical sensor(s) for receiving light from the illuminated human tissue.

Herein, when it is stated that the optical sensor module is for measuring SPG and PPG signals "at human tissue", it should be understood that the light from the first and second laser sources is incident on the human tissue, and that the one or more optical sensors are configured to receive, and measure, light which is reflected and/or scattered from the surface of the human tissue, or from components of the tissue beneath the surface, and which is transmitted back through the tissue in a reflectance measurement geometry, or light that is only transmitted through the tissue in a transmission measurement geometry. In some cases, the one or more optical sensors may be arranged, in use, to be in contact with a user's skin, in which case the light from the first light source and the second light source may enter the user's tissue through the skin, and be reflected or scattered from components of the tissue beneath the skin, and then travel back through the tissue, whereupon, on being transmitted back through the skin, it may be detected by the one or more optical sensors. In alternative cases, the one or more optical sensors may be configured to be spaced from the user's skin in use, in which case the received light may further include light which is reflected from the surface of the user's skin.

In other cases, the one or more optical sensors may be configured to receive light which has been transmitted through the tissue. In those cases, the one or more optical sensors may still be arranged, in use, either to be in contact with the user's skin or spaced from the user's skin. Transmission may, for example, be transmission from one side of a finger, ear, or toe to the other.

Some embodiments of the invention relate to illumination of organic tissue. This may be "human tissue" or "animal tissue". Herein, "human tissue" or "animal tissue" may refer to blood (e.g. blood cells or components thereof, such as the cell membranes), and elements of the vasculature (e.g. arteries, veins, capillaries, or walls thereof). It will be appreciated that different physiological parameters may be measured or otherwise determined based on illumination of different types of human tissue—this is discussed later in the application.

Optional features of the invention will now be set out. These are applicable singly or in any combination with any aspect of the invention.

Optionally, the first light source is a laser with a wavelength of operation lying within a red wavelength, which may be thought of as the range of 600 nm to 1000 nm, or the range from 620 nm to 1000 nm.

Optionally, the wavelength of operation of the laser is 660 nm or 760 nm.

Optionally, the second light source is an LED.

Optionally, the second light source is an LED operating at infra-red (IR) wavelengths (e.g. >800 nm).

Optionally, the second light source is an LED operating at a red wavelength, e.g. a wavelength within the range of 620 nm to 1000 nm.

Optionally, the first and second light sources are both lasers and are located on the same photonic integrated circuit (PIC).

Optionally, the first light source is a laser having a first wavelength, the second light source is an LED operating at a second wavelength, the optical sensor further comprising a third light source, the third light source comprising an LED operating at the first wavelength or a similar wavelength to the first wavelength.

Optionally, the first light source is a laser having a red wavelength within the range of 620 to 800 nm, the second light source is an LED operating at an IR wavelength within the range of 800 to 1000 nm, the optical sensor further comprising a third light source, the third light source comprising an LED operating at red wavelength within the range of 620 to 800 nm.

Optionally, the first and second light sources and the one or more optical sensor(s) are configured to carry out SPG and PPG measurements simultaneously or near-simultaneously.

Optionally, the one or more optical sensor(s) comprises an image sensor.

Optionally, the same image sensor is used to extract measurements from both the first light source and the second light source.

Optionally, the one or more optical sensor(s) is configured to carry out one or more of the following: in-pixel ambient/DC subtraction; near pixel ambient DC subtraction; pixel block statistics calculation; and/or pixel array statistics calculation.

Optionally, the one or more optical sensor(s) includes a processor configured to process captured data in-device and generate PPG and/or SPG output data.

Optionally, the one or more optical sensor(s) comprises an event-based image sensor.

Optionally, the one or more optical sensor(s) comprises a photodiode and separate sensor (e.g. CMOS).

Optionally, the optical sensor module further comprises one or more processors configured to convert optical measurement(s) at the one or more optical sensor(s) to measurements of one or more of the following: blood pressure, SpO2, arterial stiffness, heart rate, heart rate variability, atrial fibrillation, bradycardia, tachycardia, and/or movement such as steps taken or gestures.

Optionally, the optical sensor module may be located or locatable on a consumer wearable, typically understood to have a small form factor.

Optionally, the optical sensor may be located on or as part of a module. The module may be part of a strap or attached to a strap such that measurements are taken over the radial or ulnar arteries of the wrist.

Optionally, the optical sensor module may be located on a wrist strap of a wearable device.

Optionally, when the wearable device is located on the wrist of a user, one or more of the optical sensor(s) are located over the radial artery of the user.

Optionally, the wearable device includes a timepiece, and a strap that connects to the timepiece, and the entire optical sensor module is located on the strap. In this way, the smart strap may advantageously be used in combination with analogue timepieces. That is to say, the operation of the smart strap can be completely separate from the operation of the timepiece. This may be advantageous since there is limited space on the back of the wrist combined with user tolerance for stack height.

In addition, there remains a strong desire for analog timepieces, often in the higher price point market. Consumers must forgo health-related benefits to enjoy such timepieces, or wear two watches; a smartwatch that provides wellness/cardiovascular metrics and a quality analog timepiece.

Some embodiments of the present invention also provide for physiological benefits over prior art devices which may incorporate optical sensor(s) onto the timepiece itself to be located at the back of the wrist. The back of the wrist is actually not the ideal place from which to acquire biophotonic measurements owing to low vascularization. By moving the optical sensors to a radial or ulnar site, it is possible to better utilise PPG signals at red wavelengths and obtain SpO2 sensors with stronger performance. This results in more accurate measurements, for example of heart rate, where prior art monitors located at the back of the wrist typically use green light to access the surface capillaries and utilize the higher absorption of hemoglobin in the green wavelength range. Although red wavelengths are known for SpO2 measurements, this typically takes place at the fingertip of a user, because of the significantly higher vascularization in that location.

A smart strap according to one or more embodiments of the present invention would provide many cardiovascular parameters such as Heart Rate (HR), Heart Rate Variability (HRV), SpO2, Blood Pressure (BP). The strap may rely on a small form factor PIC, application specific integrated circuit (ASIC) and flexible electronic substrate. It is envisioned that the data for measuring the parameters can be obtained with just 2 or 3 laser wavelengths in the red and NIR regions by combining SPG and PPG information. Space is required in the strap for Bluetooth, battery, and other features normal in such a wearable device.

Optionally, the optical sensor may further comprise one or more additional light sources. In this way, the light source is configured to be capable of operating at more than two wavelengths. By providing multiple wavelengths at the sensor, it would be possible to carry out co-oximetry readings. A co-oximeter may use six or more wavelengths to measure the oxygen carrying state of haemoglobin in the blood of a user.

According to one or more embodiments of a second aspect of the present invention, there is provided, a wearable device comprising an optical sensor module according to any one of the embodiments herein.

Optionally, the wearable device may further comprise one or more additional optical sensor(s), the one or more optical sensors corresponding to the optical sensor(s) of any one of the embodiments described herein. This may, for example provide a device capable of performing co-oximetry.

According to one or more embodiments of a third aspect of the present invention, there is provided, a strap (a "smart strap") comprising an optical sensor module according to any one or more of the embodiments described herein.

According to one or more embodiments of a fourth aspect of the present invention, there is provided a wearable device comprising two or more bio-monitoring circuits, each bio-monitoring circuit comprising a respective light source and sensor. Such a wearable device could incorporate any one or more of the optional features described herein.

According to one or more embodiments of a fifth aspect of the present invention, there is provided a strap for a wearable device, the strap comprising two or more bio-monitoring circuits, each biomonitoring circuit comprising a respective light source and sensor. Such a strap could incorporate any one or more of the optional features described herein.

Further optional features of embodiments of the invention are set out below.

BRIEF DESCRIPTION OF THE DRAWINGS

Embodiments of the invention will now be described by way of example with reference to the accompanying drawings in which.

DETAILED DESCRIPTION

SPG signals are obtained from blood flow speed and are generally of larger magnitude than PPG signals at the same wavelength. Additionally, because the SPG signal is obtained primarily from deeper lying vasculature with faster flow, it is less impacted by applied pressure. The SPG signal is comprised of very sharp peaks when collected at >20 Hz and preferably >100 Hz frame rate and so provides an excellent means of measuring HR. A cardiovascular module that combines SPG and PPG signals may provide numerous cardiovascular metrics including blood pressure, SpO2, arterial stiffness, heart rate, heart rate variability, atrial fibrillation, bradycardia, and tachycardia with just red and "IR" sources. Therefore, a green LED and/or dedicated detector for visible light is not required, which saves both battery consumption and space. Furthermore, the blood flow (SPG) measurement is very sensitive to motion and provides signals that may be interpreted as steps, gestures, or other movement-related phenomena. Thus, the module may or may not include an accelerometer.

Since the hemoglobin absorption band is quite steep in the region of 600-700 nm, SpO2 accuracy depends on the accuracy of the wavelength of the red light. Devices that utilize LEDs, with resulting broadband emission and sensitivity to temperature, may come out of calibration and give erroneous results. SPG signals require a coherent laser as light source. Lasers have much narrower emissions and less sensitivity to temperature, thereby providing a more accurate SpO2 over a wide range of conditions. Note that the "IR" light source (>800 nm) may be broader because haemoglobin absorption is relatively flat in the region 830-900 nm.

The image sensor can incorporate methods of in-pixel cancellation of DC light signals (from non-pulsatile light) or light from the ambient environment. In some embodiments, an event camera sensor may be used in place of a conventional image sensor for the detection of the SPG and PPG signals. Such a sensor offers advantages in lower power usage and processing requirements due to its capability of providing pixel change updates instead of full frame updates.

In some embodiments, the invention includes, but is not limited to a cardiovascular module that provides blood pressure, SpO2, arterial stiffness, heart rate, heart rate variability, atrial fibrillation, bradycardia, and tachycardia parameters, in a wearable, compact form factor. This module is optimized for both PPG and SPG signal collection to obtain robust measurements.

Figure 1:
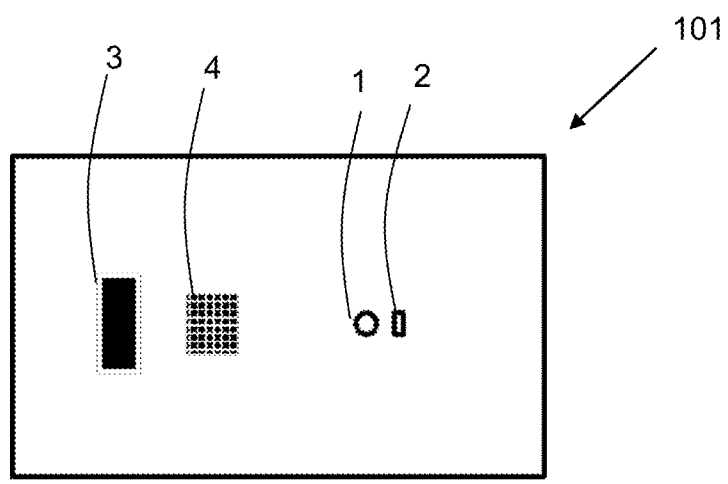
FIG. 1 shows a schematic diagram of an optical sensor module according to an embodiment of the present invention.

FIG. 1 shows an optical sensor module, 101 comprising a first light source 1, for illuminating the human tissue for use with SPG measurements. In this embodiment, the first light source is a laser having sufficient coherence length to acquire SPG signals (e.g. vertical-cavity surface-emitting laser (VCSEL), distributed feedback (DFB) diode, distributed Bragg reflector (DBR) diode, volume holographic (VHG) diode).

The optical sensor module also includes a second light source 2 for illuminating the human tissue for use with PPG measurements. In the embodiment shown, the second light source takes the form of an infra-red LED (e.g. having a center wavelength of 830-980 nm).

Including the second light source in the form of an LED may be advantageous as it is less susceptible to error due to wavelength drift owing to the flat hemoglobin spectrum in that region.

A plurality of optical sensor(s) is also located on the optical module for receiving light from the illuminated human tissue. In this embodiment, these sensors include a photodiode, 3 and a CMOS image sensor, 4. The photodiode may take the form of a large area photodiode with DC subtraction electronics. Electronics for the photodiode are present and may be optimized for PPG data collection to obtain SpO2 whereas the CMOS sensor may be utilized for the SPG signal collection to obtain BP and other cardiovascular parameters. This embodiment does not contain a green LED, although it would be possible to adapt it (not shown) to include a green or other wavelength LED or laser either in addition, or as a replacement to the components shown in FIG. 1.

Figure 2:
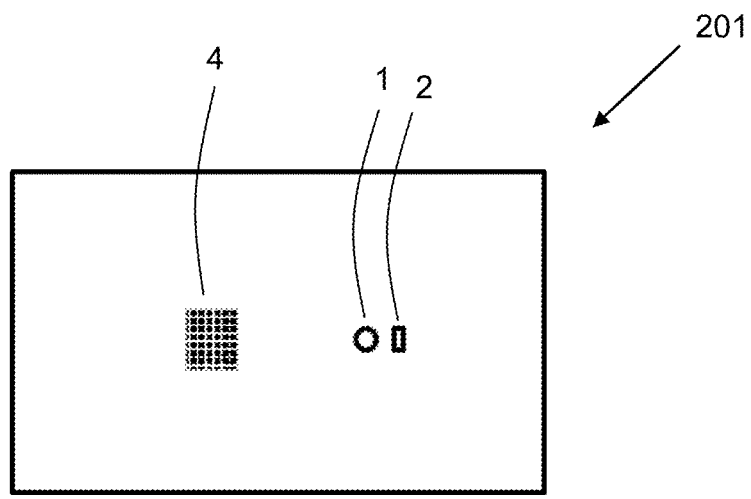
FIG. 2 shows a schematic diagram of an optical sensor module according to a further embodiment of the present invention.

An optical sensor module, 201 according to a second embodiment is described below in relation to FIG. 2, the second embodiment, differing from the embodiment of FIG. 2 in that the photodiode 3 is removed, and the PPG signal is instead obtained using an image sensor.

The image sensor may be a charge-coupled device (CCD), a CMOS image sensor (CIS), or an implementation of a CCD or CIS incorporating an in-pixel DC (non-pulsatile) or ambient light subtraction method such as but not limited to auto-zeroing and chopping, common mode reset, minimum charge transfer, or dual transfer gate architecture.

Alternatively, the image sensor may be an event image sensor (EIS) which produces asynchronous pixel updates according to defined pixel intensity changes as opposed to conventional synchronous frame-based CCD or CIS sensors.

Figure 3:
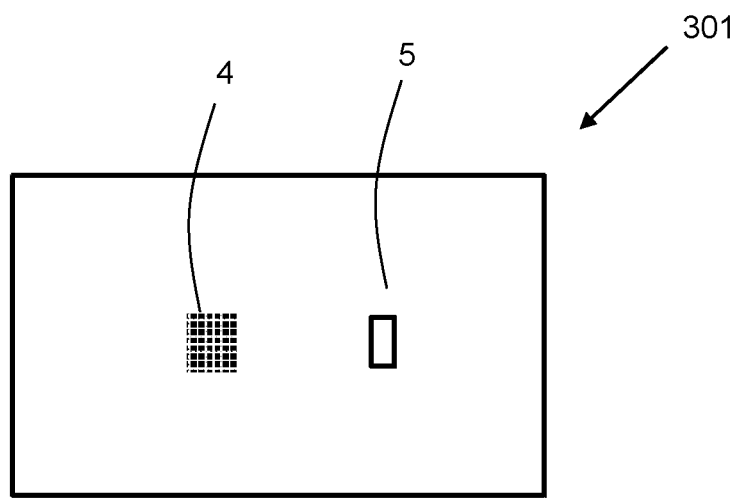
FIG. 3 shows a schematic diagram of an optical sensor module according to a further embodiment of the present invention.

A third embodiment of an optical sensor module 301 is described below with reference to FIG. 3. In this embodiment, both the first and second light source are lasers. The module comprises only the image sensor described in the second embodiment and a photonic integrated chip (PIC) 5 containing at least two lasers, one laser having a red wavelength and one laser having a NIR/IR wavelength. Red wavelength may be taken to be light with a wavelength from 620 nm to 800 nm. NIR/IR may be taken to be light with a wavelength of 800 nm to 1000 nm. The PIC may, in addition, contain multiple laser wavelengths to also perform CO-oximetry (carboxyhemoglobin, methemoglobin, etc). As with the embodiment of FIG. 2, a single image sensor is used to detect both PPG and SPG signals.

Any one or more of the embodiments described herein may utilize temporary speckle mitigation techniques for the collection of the PPG signal obtained from a photodiode, such as a deformable mirror to rapidly adjust optical pathlengths, an optical phase array, raster scanning, angle scanning, wavelength scanning or broadening, or any combination thereof. This may improve SNR as it reduces speckle noise from the intensity signal, which is more important as the size of the sensor/detector is reduced. Additionally, or alternatively, multiple photodiode acquisitions of the laser signal may be collected and averaged to improve SNR.

Any one or more of the embodiments may also include a multi-aperture array in front of the image sensor to improve SNR while maintaining the appropriate speckle to pixel ratio by virtue of the aperture diameters and distance from the sensor. Such a sensor does not require a lens to obtain the appropriate speckle to pixel ratio, although a lens or lens array may be used in conjunction with the aperture plate.

It is to be understood that the embodiments described are not limitations, e.g. green, blue, yellow, or other wavelength LEDs or lasers may be included and any LED may be replaced with a laser. The SPG signal requires, at minimum, one laser of any wavelength be present in the system along with at least one image sensor. Alternatively, in place of an image sensor that is required for speckle spatial contrast measurements, the SPG signal may be obtained by diffuse correlation spectroscopy (DCS) or interferometric diffuse correlation spectroscopy (iDCS). DCS or iDCS requires either a photodiode or balanced receiver with >500 kHz sampling rate or a single photon counting avalanche detector (SPAD) detector.

Additional modalities may be added to this module, such as ECG (electrocardiography) sensor(s), which may be utilized in addition to the SPG and/or PPG signals to calculate pulse arrival times to aid in BP estimations. ECG may also be utilized for certain arrythmia detections as part of the suite of cardiovascular parameters.

Figure 4A:
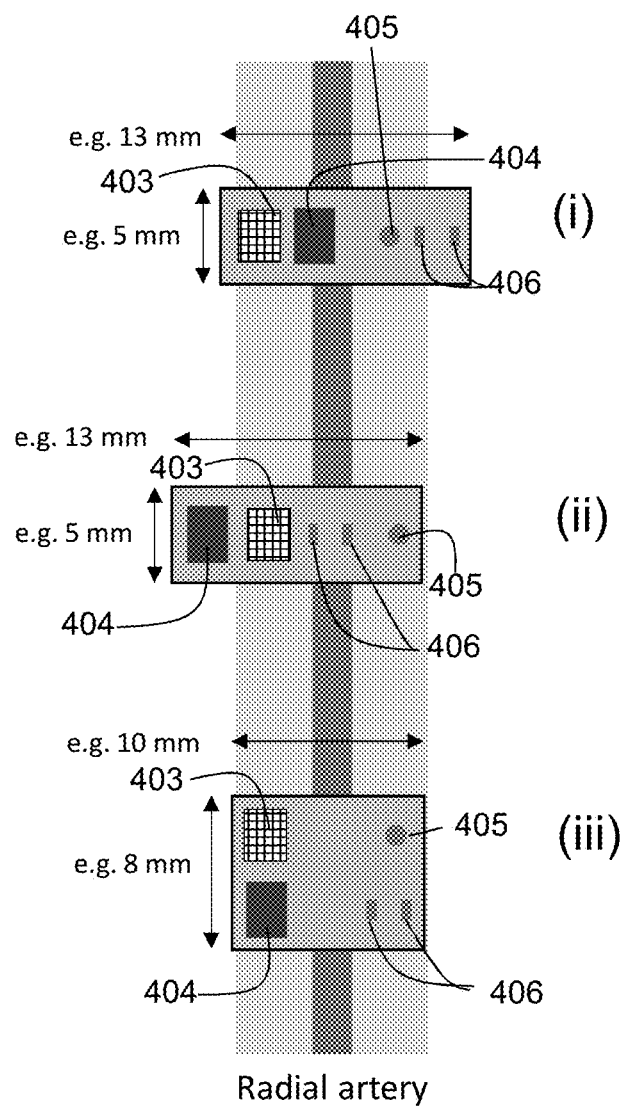
FIGS. 4A and 4B each show a schematic diagram of three further optical sensor modules according to further embodiments of the present invention.
Figure 4B:
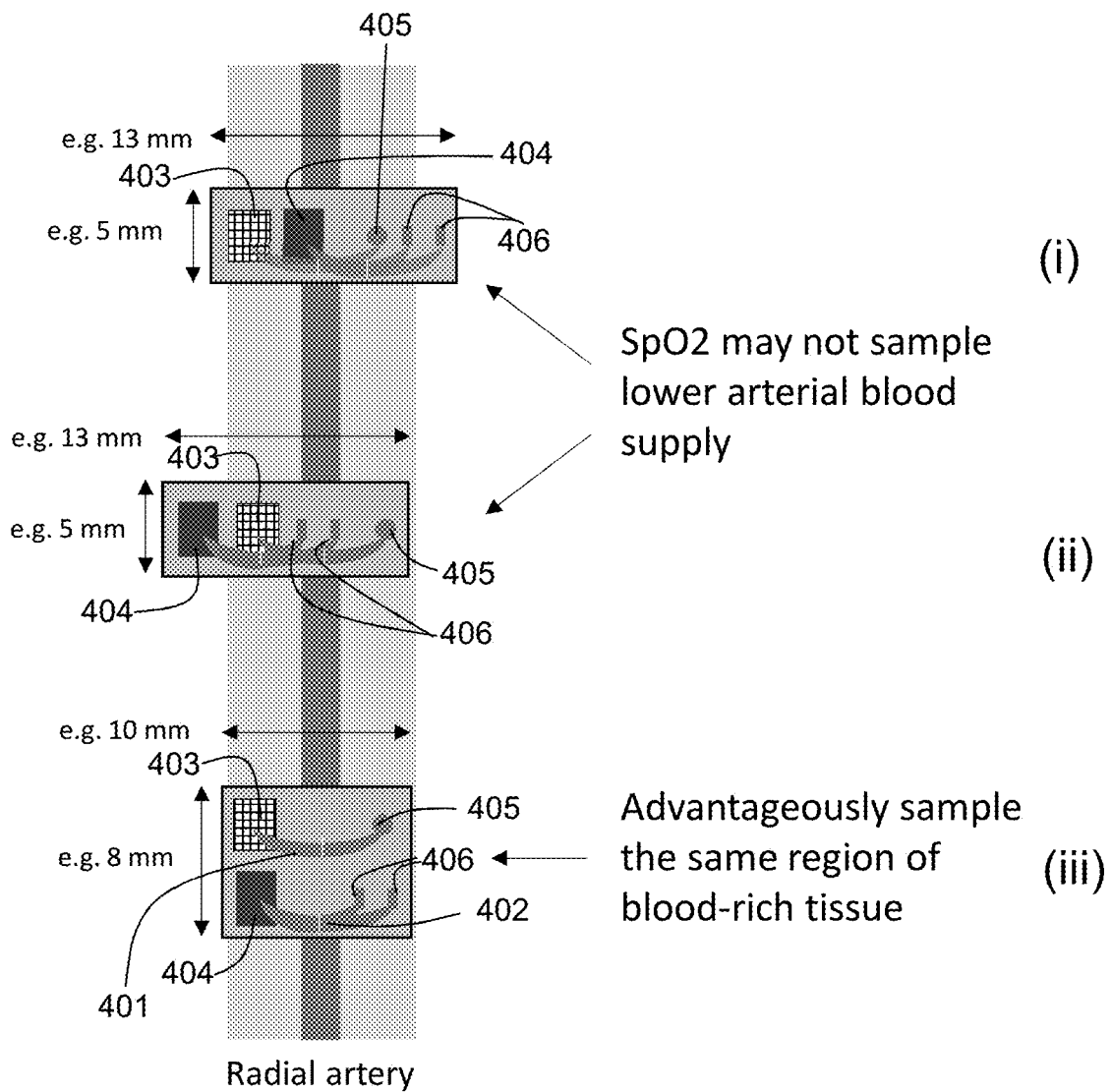

Three further optical modules are shown in FIGS. 4A and 4B. FIG. 4B differs from FIG. 4A in that it shows the link between each light source and its respective detector. Each module ((i), (ii), (iii)) includes an image sensor 403 (e.g. a CMOS image sensor (CIS)), a second sensor 404 (e.g. a photodiode), a laser (e.g. a VCSEL), and one or more LEDs (e.g. a red and an infra-red LED). A module may take the form of discrete components mounted to a printed circuit board assembly (PCBA). Example dimensions are shown and are approximate, based on discreet component sizes. However, it is important to note that these are only illustrative examples, and that other sizes would be possible.

Placement may be over an artery, 15, such as the radial or arterial artery. The arrangement shown in FIG. 4A (iii) (and corresponding FIG. 4B (iii)) is advantageous as the artery passes in the middle of the space, or "banana" (401, 402) formed between the source and detector for both the SPG and PPG modules. In the particular embodiment shown, the SPG and PPG modules are located separately on the same printed circuit board assembly (PCBA), with the PPG module corresponding to the LED(s) and photodiode, and the SPG module corresponding to the laser (e.g. VCSEL) and the image sensor (e.g. CIS).

It has been found to be advantageous for the modules to be stacked vertically with respect to an artery (i.e. along the artery when in use) in order to maximize light of similar source-detector separation. Again, such an arrangement is shown in FIG. 4A (iii) and FIG. 4B (iii).

Figure 5:
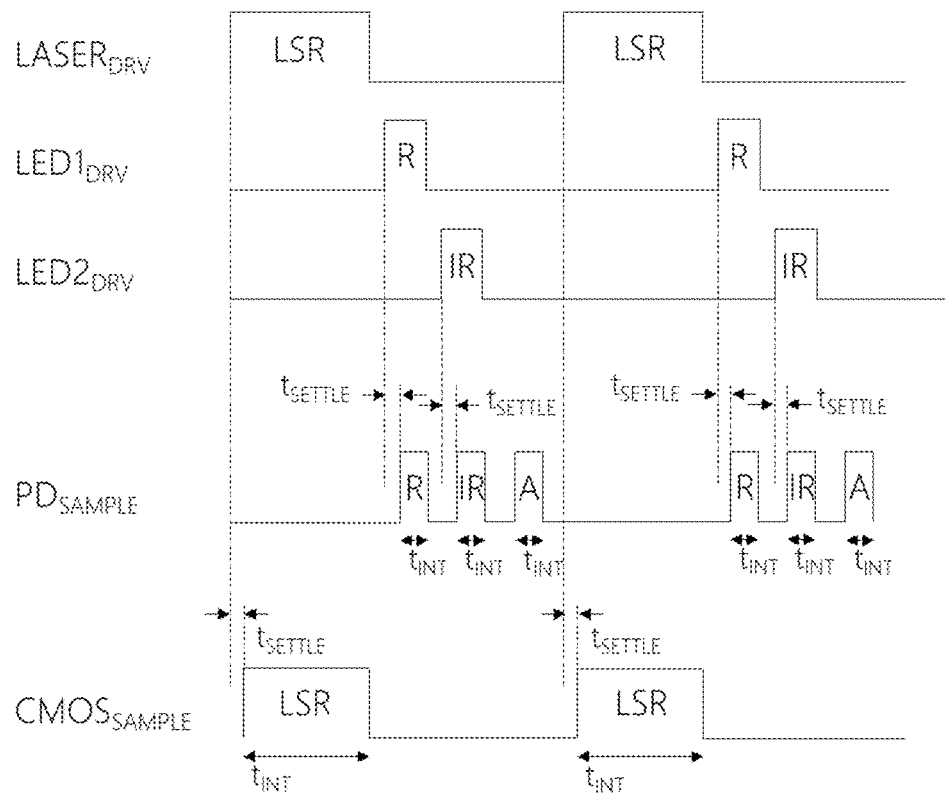
FIG. 5 shows a representation of module operation according to a first example.

A first example of module operation is described below in relation to FIG. 5. In this example, a first laser has a wavelength of 785 nm and separate LEDs having red (660 nm) and IR (900 or 940 nm) wavelengths respectively are also present. This gives a total of three different wavelengths used to interrogate the surface. In the example shown, the LED data acquisition is fitted within the period after camera integration ($t_{INT}$) and before max frame rate, assuming that the camera integration time is less than the period required for max frame rate operation. A time delay $t_{SETTLE}$ is also shown on FIG. 5, this time delay being caused by laser or light intensity stabilisation.

Figure 6:
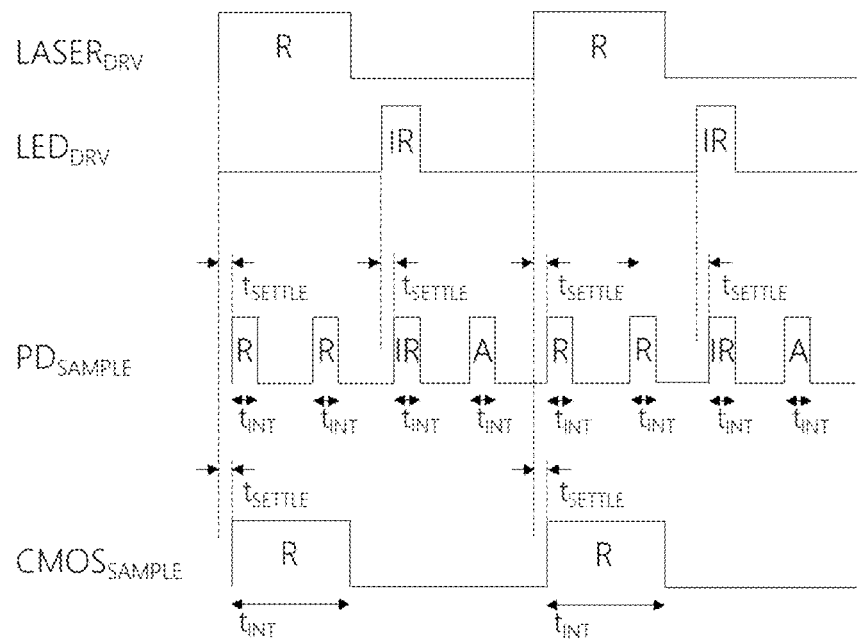
FIG. 6 shows a representation of module operation according to a second example.

A further example is shown in FIG. 6, the optical module comprising a single laser and a single LED, thereby operating at two wavelengths. The laser generates light of a red (e.g. 660 nm) wavelength and the LED generates light of an IR (e.g. 900 or 940 nm) wavelength.

For convenience, operation parameters can be chosen to keep sampling rate of the IR signal the same for the PD and to use the photodiode to acquire multiple collections of the red laser in order to improve SNR due to speckle noise. Depending on the integration times used, it may be possible to carry out two or more red PD acquisitions.

Figure 7:
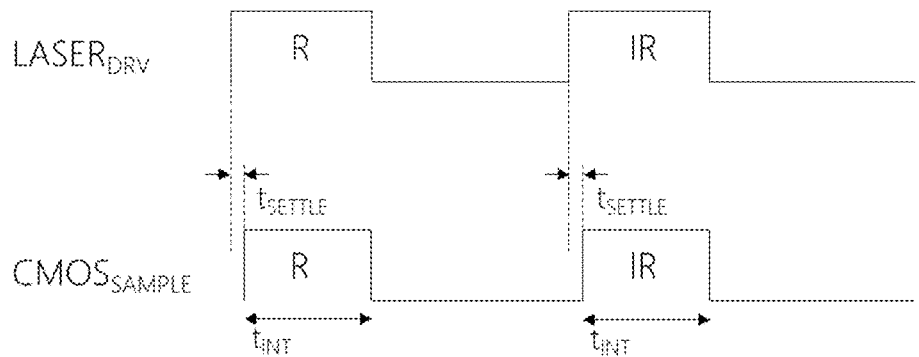
FIG. 7 shows a representation of module operation according to a third example.

A third example of an operation of an optical module is shown in FIG. 7. In this embodiment, the optical module includes a laser module or PIC configured to generate light of two different wavelengths (R and IR), and a single sensor such as a CMOS image sensor. Integration of the signal ($t_{INT}$) by the sensor starts at a time ($t_{SETTLE}$) after the start of the irradiation of the sample by the laser. The PIC may contain two lasers to generate both red (660 nm) and IR (960 nm) light. It is possible that more than two wavelengths may be generated by the PIC, in which case the operation shown in FIG. 7 can be applied, and each wavelength cycled through in a given order.

Figure 8:
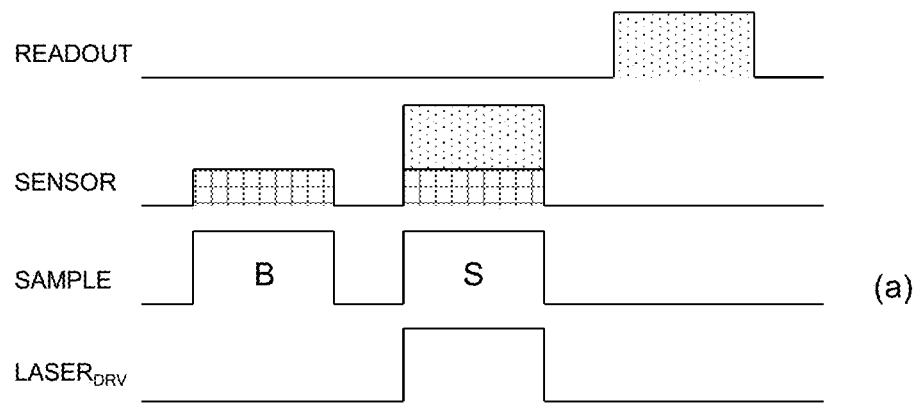
FIG. 8 depicts (a) an illustration of the operation of in-pixel ambient/DC removal, and (b) an illustration of the operation of an event image sensor.
Figure 8:
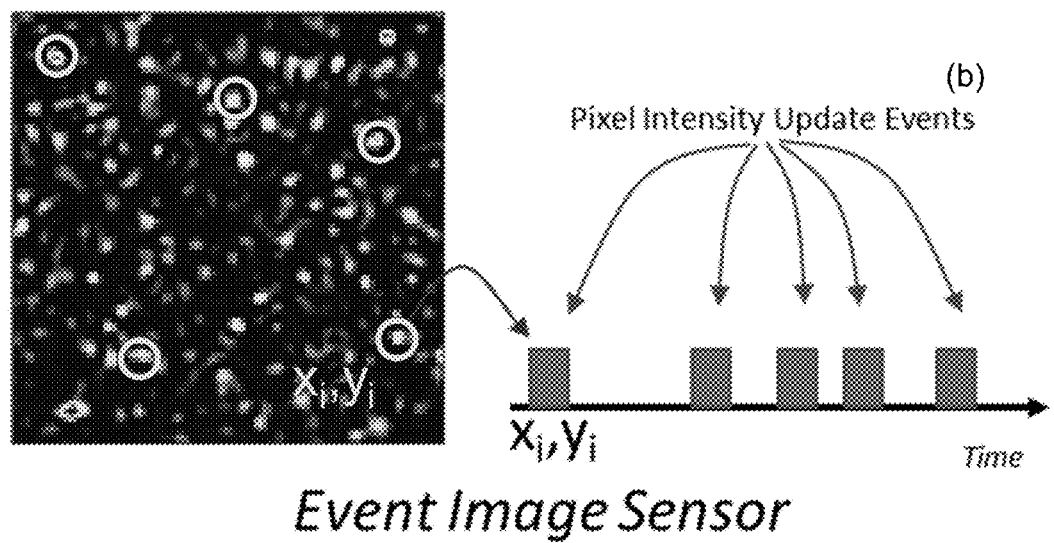

A method by which the sensor can mitigate the effect of ambient background light is shown in FIG. 8.(a). The sensor can sample (SAMPLE-B) the ambient background light with the laser drive off (LASERDRV). The sensor can subsequently sample with the laser on (SAMPLE-S), the resulting reading being a combination of the signal and the ambient background light. Subtraction of the two readings results in a readout (READOUT) consisting of only the contribution of the signal. The subtraction can be accomplished by, but not limited to, in pixel charge subtraction or post-photoconversion voltage subtraction.

An example of a speckle pattern measured by an event based imaging device is shown in FIG. 8.(b). The event based image sensor functions by the detection of discrete changes in pixel intensity (events). The temporal fluctuation of the set of speckle pebbles (xi,yi) translates to the generation of an asynchronous series of pixel events, These events can then be processed by either, but not limited to, integration over a fixed time interval to create a corresponding frame of pixel intensities or in an online fashion by which a histogram of pixel update event rates relates to the temporal fluctuation of the speckle pattern.

Figure 9:
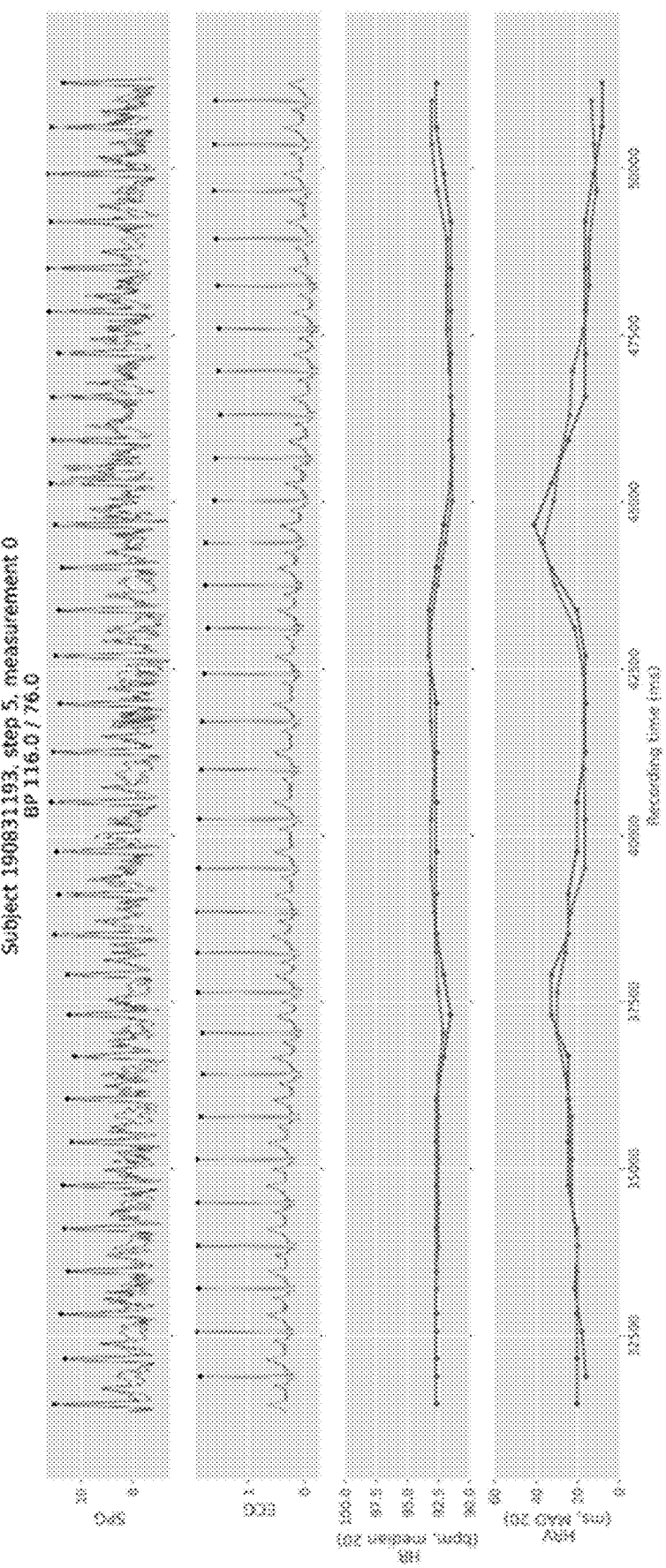
FIG. 9 depicts SPG and ECG data from a first subject.
Figure 10:
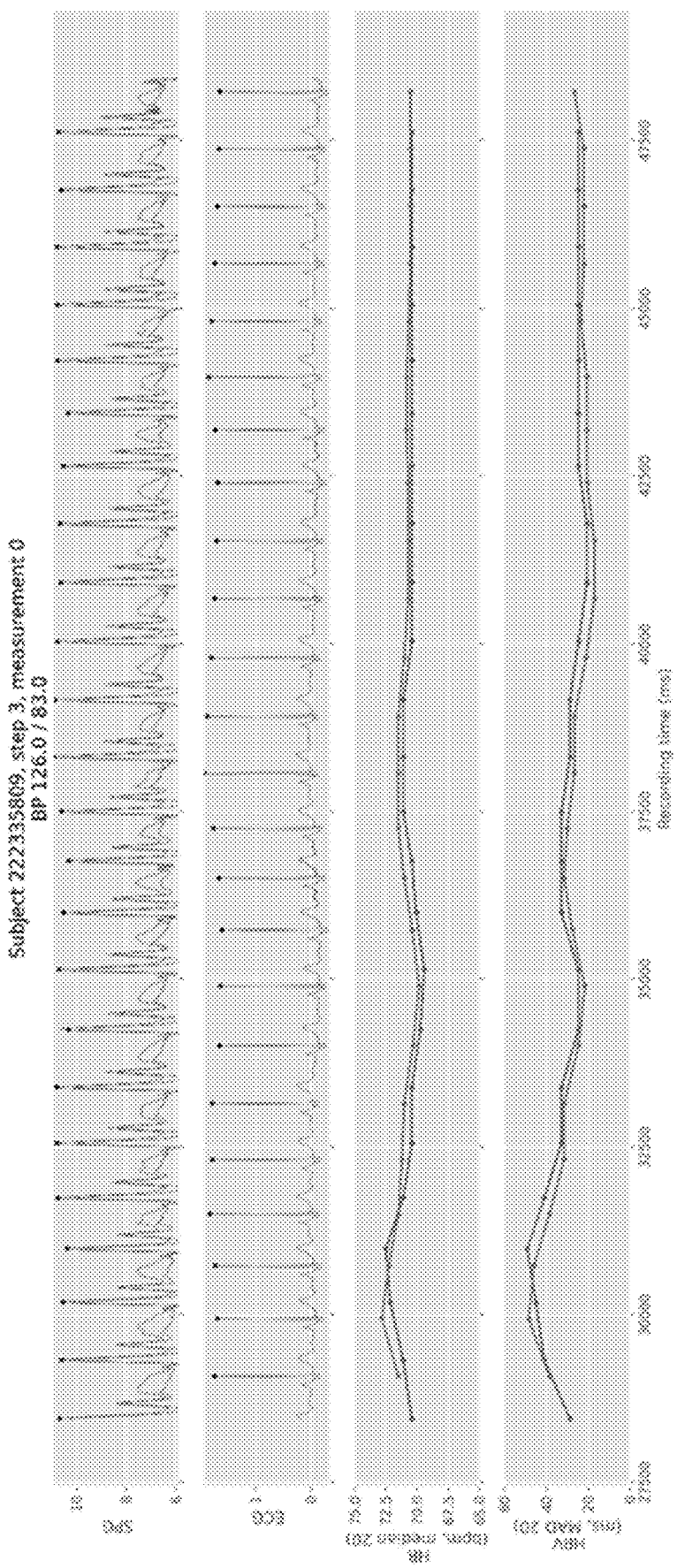
FIG. 10 depicts SPG and ECG data from a second subject.

Examples of SPG (top) and ECG (second from top) data from two subjects are shown in FIGS. 9 and 10 respectively, the data showing equivalency in performance of measuring HR (third from top) and HRV (bottom).

Figure 11:
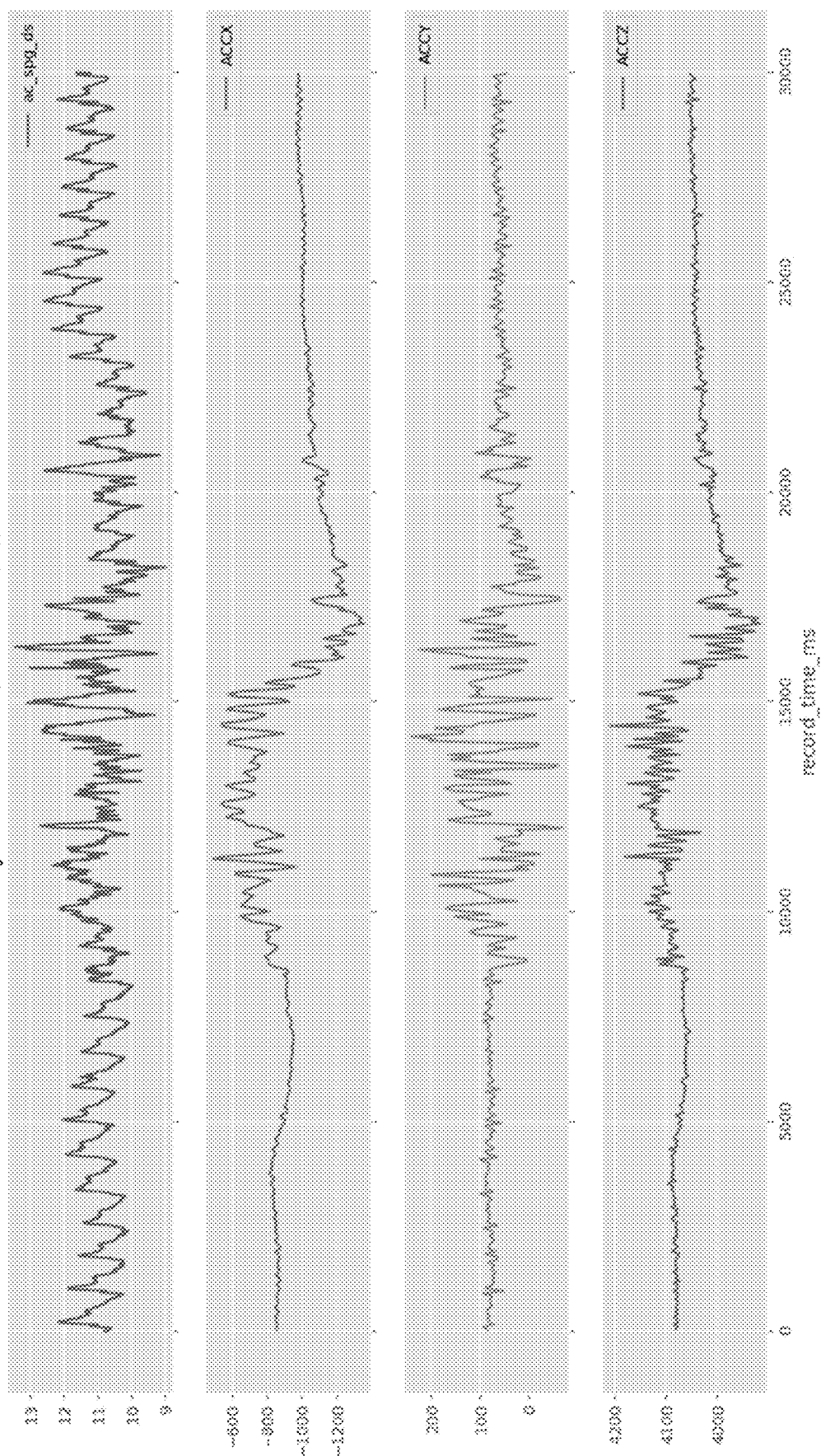
FIG. 11 depicts SPG data from a third subject.
Figure 12:
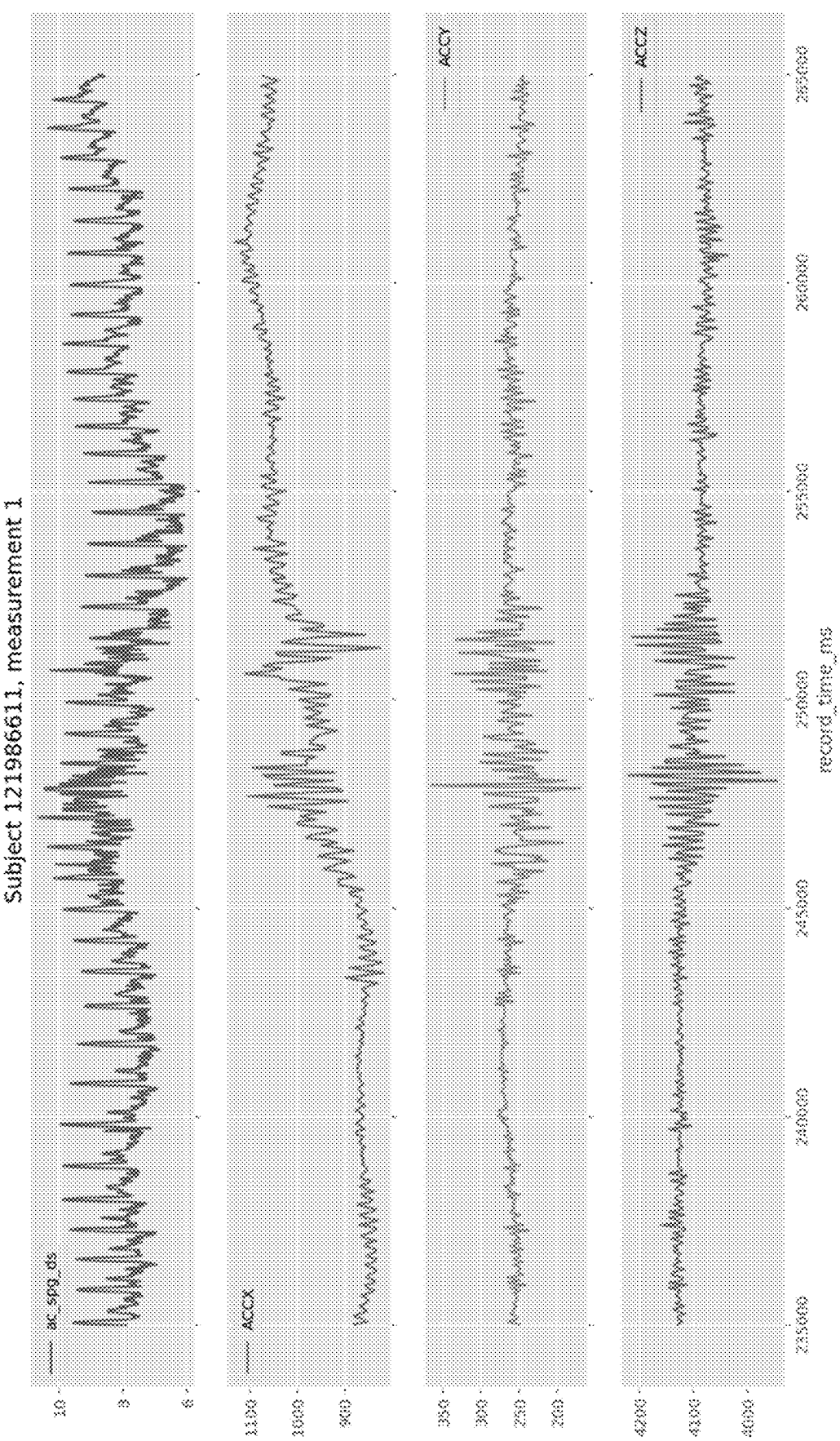
FIG. 12 depicts SPG data from a fourth subject.

Examples of SPG signals (top) contain both high and low-frequency components of accelerometer data (X, Y, and Z axes in second, third, and fourth plots from the top) are shown in FIGS. 11 and 12 for two respective subjects. Motion detection and tracking may be achieved via the SPG signal and without the need for an accelerometer.

Figure 13:
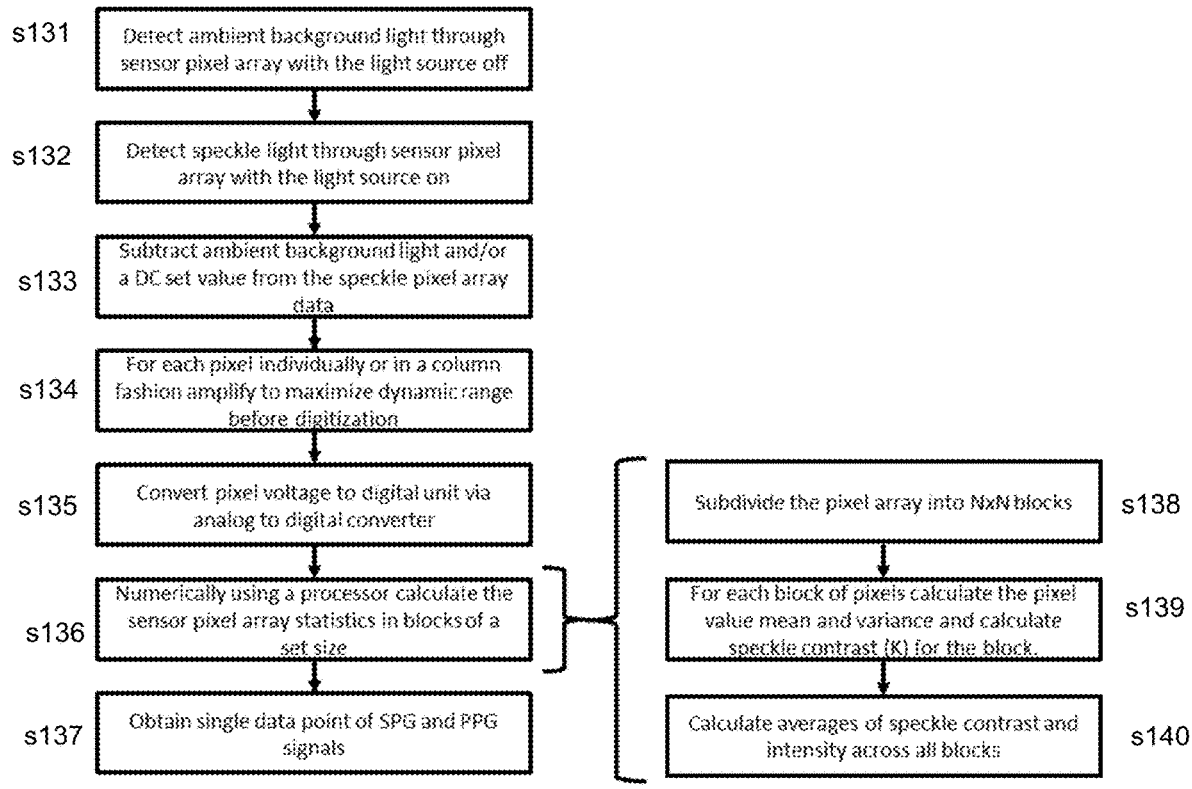
FIG. 13 depicts an example process followed where the optical sensor module of some embodiments of the present invention is configured to carry out pixel array statistics.
Figure 14:
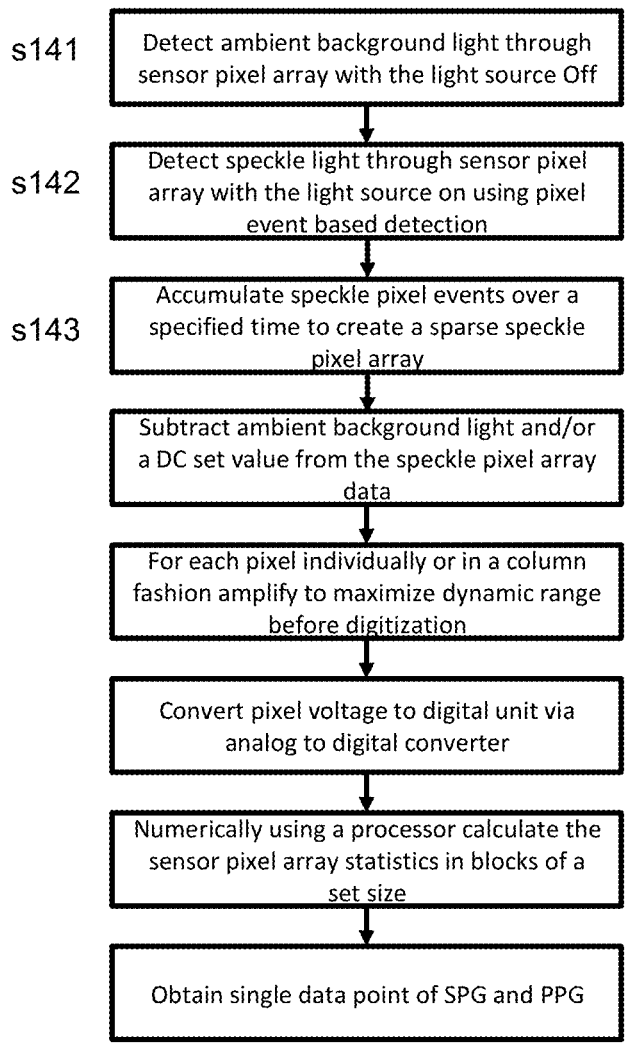
FIG. 14 depicts an example process followed where the optical sensor module of some embodiments of the present invention is configured to carry out event-based detection.

The processing of data from one or more sensor pixel arrays can be better understood with reference to the flow diagrams shown in FIGS. 13 and 14.

In the embodiment shown in FIG. 13, a sensor pixel array is first used to detect ambient background light with the light source turned off (s131). Speckle light is then detected (s132) by the sensor pixel array, when the light source is turned on. Ambient background light can then be subtracted and/or a DC set value can be subtracted from the speckle pixel array data (s133). For each pixel individually, or in a column fashion, amplification (s134) may be carried out to maximize the dynamic range of the data before digitization (s135). At digitization, pixel voltage is converted to digital unit via an analogue to digital converter. A processor may then calculate (s136) the sensor pixel array statistics, and may do so in blocks of a set size. Once these statistics have been calculated, a single data point can be obtained (s137), the single data point corresponding to SPG and PPG signals.

Calculation (s136) of the sensor pixel array statistics may include the steps of: subdividing (s138) the pixel array into N×N blocks; for each block, calculating (s139) the pixel value mean and variance and calculating speckle contrast (K) for the block; and calculating (s140) averages of speckle contrast and intensity across all blocks.

A process including event-based detection is described below in relation to FIG. 14. The process differs from that described above in relation to FIG. 13 in that the first two steps (s131, s132) are replaced by three new steps (s141, s142, s143). Firstly, ambient background light is detected (s141) through the sensor pixel array with the light source off, then speckle light is detected (s142) through the pixel array with the light source on. This may be achieved by pixel event-based detection. Next, speckle pixel events are accumulated (s. 143) over a specified time, to create a sparse speckle pixel array.

In one or more embodiments of the present invention, the optical sensor module is located on a wrist strap 1501 of a wearable device. In some of these embodiments, the optical sensor module is entirely located on a smart strap, the smart strap being a strap that includes all of the electronics and processing required by the optical sensor and can thus function completely separately from any timepiece that is to be connected to the strap. In this way, the smart strap may be used in combination with (e.g. by retrofitting onto) any pre-existing timepiece including analogue timepieces.

Figure 15:
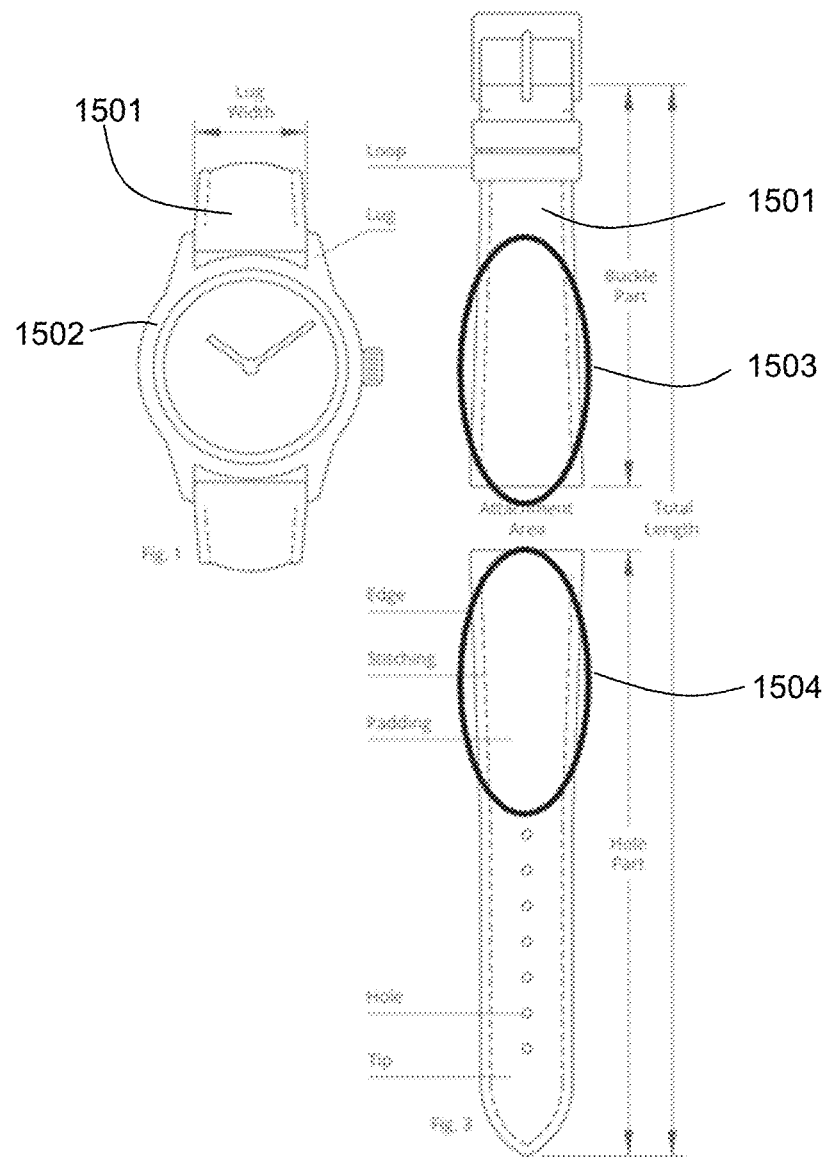
FIG. 15 depicts a smart strap comprising an optical sensor according to some embodiments of the present invention, the smart strap being made of a non-conductive material.

A first smart strap is shown in FIG. 15, the smart strap 1501 being connectable to a timepiece 1502. This embodiment is typical of non-metal (e.g. leather) straps. The optical sensor module may be located within a region 1503, 1504 on one or both sides of the strap such that the optical sensors lie over the radial and/or ulnar artery (arteries) of the user.

Figure 16:
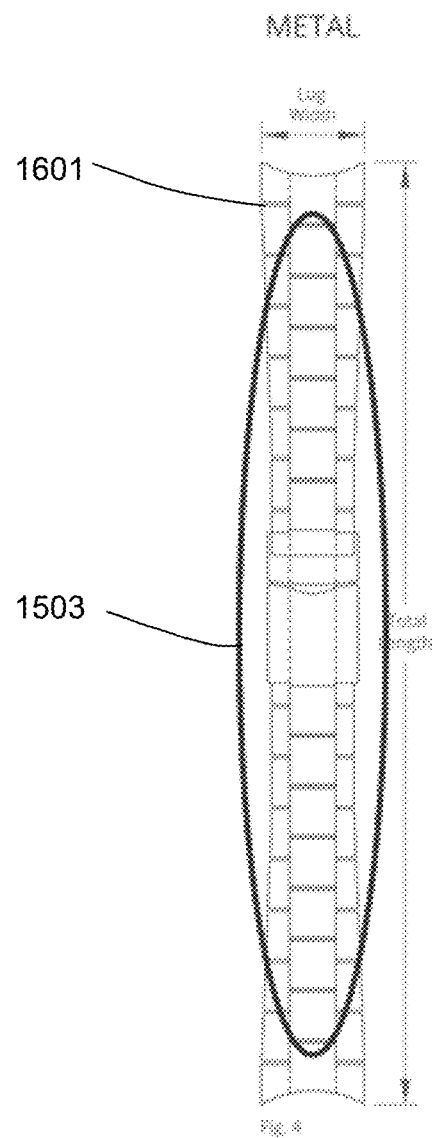
FIG. 16 depicts a smart strap comprising an optical sensor according to some embodiments of the present invention, portions of the smart strap being made of a conductive material.

In an alternative smart strap shown in FIG. 16, the smart strap 1601 is made of a conductive material such as metal. Again, components of the optical sensor module may be located along the strap, and typically along the entire region 1603 of the strap. Any optical sensors of the optical sensor module may be placed so that when the conductive strap (or portionally conductive strap) is in use, being worn by the user, the one or more sensors are located above the radial and/or ulnar artery (arteries) of the user.

On a conductive (or portionally conductive), metal strap, the possibility exists for the sensing and electronic elements such as battery, Bluetooth, etc to be spread out, using the clasp (volar wrist) or other contact points along the strap as an electrical connection It is possible to optimally design a strap using any external material (leather, silicone, plastic, metal) with sensing and electronics fully enclosed within and using the clasp for electrical attachment. The attachment area (dorsal wrist to timepiece/smartwatch) would be standard lug or compression spring or other common attachment mechanism.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

All references referred to above are hereby incorporated by reference.

The invention claimed is:

1. A wearable device comprising an optical sensor module, the optical sensor module comprising:
   a light source comprising a laser, the light source being configured to selectively apply speckle mitigation techniques to light generated by the laser and to illuminate tissue;
   an image sensor configured to selectively receive, through the tissue, a first light signal from the light source when the light source does not apply the speckle mitigation techniques;
   a photodiode configured to selectively receive, through the tissue, a second light signal from the light source when the light source does apply the speckle mitigation techniques; and a processor configured to process first data, corresponding to the first light signal, to generate a speckleplethysmography (SPG) measurement, and to process second data, corresponding to the second light signal, to generate a photoplethysmography (PPG) measurement.

2. The wearable device of claim 1, wherein the image sensor is configured to carry out in-pixel DC subtraction.

3. The wearable device of claim 1, wherein the image sensor is configured to carry out a pixel block statistics calculation or a pixel array statistics calculation.

4. The wearable device of claim 1, wherein the light source is configured to apply the speckle mitigation techniques via a deformable mirror, an optical phase array, raster scanning, angle scanning, wavelength scanning, wavelength broadening, or any combination thereof.

5. The wearable device of claim 1, including a wrist strap, the optical sensor module being coupled to the wrist strap.

6. A wearable device comprising an optical sensor module, the optical sensor module comprising:
   a light source comprising a laser and being configured to illuminate tissue;
   one or more optical sensors configured to respectively receive, through the tissue, one or more light signals from the light source, the one or more optical sensors including an image sensor configured to carry out in-pixel DC light subtraction to subtract out a non-pulsatile component of a first light signal of the one or more light signals; and
   a processor configured to process data to generate a speckleplethysmography (SPG) measurement and a photoplethysmography (PPG) measurement, the data corresponding to the one or more light signals.

7. The wearable device of claim 6, wherein the image sensor is configured to receive, through the tissue, the one or more light signals from the light source.

8. The wearable device of claim 6, wherein the light source is configured to selectively apply speckle mitigation techniques to light generated by the laser.

9. The wearable device of claim 8, wherein the one or more optical sensors are configured to selectively receive the one or more light signals.

10. The wearable device of claim 6, the optical sensor module comprising:
    a coherent optical output configured to illuminate tissue with coherent light; and
    an incoherent optical output configured to illuminate the tissue with incoherent light,
    wherein the laser is configured to generate light at the coherent optical output, and the optical sensor module is configured to apply one or more speckle mitigation techniques to light generated by the laser to provide light at the incoherent optical output,
    wherein the image sensor is configured to receive, through the tissue, the first light signal from the coherent optical output and a second light signal from the incoherent optical output, and
    wherein the optical sensor module is configured to process first data and second data to respectively generate (SPG) the SPG measurement and the PPG measurement, the first data corresponding to the first light signal, and the second data corresponding to the second light signal.

11. The wearable device of claim 10, wherein the image sensor includes a CMOS image sensor.

12. The wearable device of claim 10, wherein the image sensor includes an event-based camera.

13. The wearable device of claim 10, wherein
    the image sensor is configured to carry out a pixel block statistics calculation or a pixel array statistics calculation.

* * * * *